(12) United States Patent
Ehr et al.

(10) Patent No.: US 6,398,709 B1
(45) Date of Patent: Jun. 4, 2002

(54) ELONGATED MEMBER FOR INTRAVASCULAR DELIVERY OF RADIATION

(75) Inventors: Timothy G.J. Ehr, Elk River; Sherri Henkemeyer, St. Cloud; Michael J. Urick, Rogers; Jeffrey H. Vogel, Brooklyn Park, all of MN (US)

(73) Assignee: SciMed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 09/420,677

(22) Filed: Oct. 19, 1999

(51) Int. Cl.⁷ .................................................. A61N 5/00
(52) U.S. Cl. ............................................................. 600/3
(58) Field of Search ........................................ 600/1–8

(56) References Cited

U.S. PATENT DOCUMENTS

| | | |
|---|---|---|
| 2,546,761 A | 3/1951 | Loftus |
| 2,862,108 A | 11/1958 | Meilink |
| 2,955,208 A | 10/1960 | Stevens |
| 3,060,924 A | 10/1962 | Rush |
| 3,147,383 A | 9/1964 | Prest |
| 3,324,847 A | 6/1967 | Zoumboulis |
| 3,505,991 A | 4/1970 | Hellerstein et al. |
| 3,643,096 A | 2/1972 | Jeffries, Jr. et al. |
| 3,669,093 A | 6/1972 | Sauerwein et al. |
| 3,674,006 A | 7/1972 | Holmer |
| 3,750,653 A | 8/1973 | Simon |
| 3,811,426 A | 5/1974 | Culver et al. |
| 3,861,380 A | 1/1975 | Chassagne et al. |
| 3,866,050 A | 2/1975 | Whitfield |
| 3,927,325 A | 12/1975 | Hungate et al. |
| 4,096,862 A | 6/1978 | DeLuca |
| 4,220,864 A | 9/1980 | Sauerwein et al. |
| 4,225,790 A | 9/1980 | Parsons, Jr. et al. |
| 4,244,357 A | 1/1981 | Morrison |
| 4,281,252 A | 7/1981 | Parsons, Jr. et al. |
| 4,314,157 A | 2/1982 | Gaines |
| 4,364,376 A | 12/1982 | Bigham |
| 4,584,991 A | 4/1986 | Tokita et al. |
| 4,588,395 A | 5/1986 | Lemelson |
| 4,631,415 A | 12/1986 | Sauerwein et al. |
| 4,702,228 A | 10/1987 | Russell, Jr. et al. |
| 4,706,652 A | 11/1987 | Horowitz |
| 4,763,642 A | 8/1988 | Horowitz |
| 4,763,671 A | 8/1988 | Goffinet |
| 4,782,834 A | 11/1988 | Maguire et al. |

(List continued on next page.)

FOREIGN PATENT DOCUMENTS

| | | |
|---|---|---|
| CA | 2166915 A | 8/1996 |
| DE | 91 02 312.2 | 8/1992 |
| DE | 195 26 680 A1 | 1/1997 |
| DE | 197 54 870 A1 | 8/1998 |
| DE | 197 24 223 C1 | 12/1998 |

(List continued on next page.)

OTHER PUBLICATIONS

Tjho–Heslinga et al., "Results of ruthenium irradiation of uveal melanoma," *Radiothereapy Oncology*, vol. 29, pp. 33–38, 1993.

Lommatzsch et al., "Radiation effects on the optic nerve observed after brachytherapy of choroidal melanomas with 106Ru/106Rh plaques", *Graefe's Arch. Clin. Exp. Ophthalmology* vol. 232, pp. 482–487, 1994.

(List continued on next page.)

*Primary Examiner*—Samuel G. Gilbert
(74) *Attorney, Agent, or Firm*—Crompton, Seager & Tufte, LLC (57) ABSTRACT

A radioactive source for use in intravascular treatment includes an elongated wire having a first diameter and an integral distal end having a second diameter. The second diameter is less than the first diameter. A plurality of spaced apart toroidal elements are disposed on the distal end of the wire. The toroidal elements include radioactive material.

18 Claims, 6 Drawing Sheets

U.S. PATENT DOCUMENTS

| | | |
|---|---|---|
| 4,784,116 A | 11/1988 | Russell, Jr. et al. |
| 4,815,449 A | 3/1989 | Horowitz |
| 4,819,618 A | 4/1989 | Liprie |
| 4,851,694 A | 7/1989 | Rague et al. |
| 4,861,520 A | 8/1989 | van't Hooft et al. |
| 4,881,937 A | 11/1989 | van't Hooft et al. |
| 4,897,076 A | 1/1990 | Puthawala et al. |
| 4,936,823 A | 6/1990 | Colvin et al. |
| 4,963,128 A | 10/1990 | Daniel et al. |
| 4,969,863 A | 11/1990 | van't Hooft et al. |
| 4,976,266 A | 12/1990 | Huffman et al. |
| 4,976,680 A | 12/1990 | Hayman et al. |
| 4,976,690 A | 12/1990 | Solar et al. |
| 5,030,194 A | 7/1991 | Van't Hooft |
| 5,032,113 A | 7/1991 | Burns |
| 5,059,166 A | 10/1991 | Fischell et al. |
| 5,084,001 A | 1/1992 | Van't Hooft et al. |
| 5,084,002 A | 1/1992 | Liprie |
| 5,092,834 A | 3/1992 | Bradshaw et al. |
| 5,103,395 A | 4/1992 | Spako et al. |
| 5,106,360 A | 4/1992 | Ishiwara et al. |
| 5,120,973 A | 6/1992 | Rohe et al. |
| 5,139,473 A | 8/1992 | Bradshaw et al. |
| 5,141,487 A | 8/1992 | Liprie |
| 5,147,282 A | 9/1992 | Kan |
| 5,163,896 A | 11/1992 | Suthanthiran et al. |
| 5,176,617 A | 1/1993 | Fischell et al. |
| 5,183,455 A | 2/1993 | Hayman et al. |
| 5,199,939 A | 4/1993 | Dake et al. |
| 5,213,561 A | 5/1993 | Weinstein et al. |
| 5,267,960 A | 12/1993 | Hayman et al. |
| 5,282,781 A | 2/1994 | Liprie |
| 5,302,168 A | 4/1994 | Hess |
| 5,344,383 A | 9/1994 | Liping |
| 5,354,257 A | 10/1994 | Roubin et al. |
| 5,370,685 A | 12/1994 | Stevens |
| 5,391,139 A | 2/1995 | Edmundson |
| 5,395,300 A | 3/1995 | Liprie .................. 600/3 |
| 5,405,309 A | 4/1995 | Carden, Jr. |
| 5,409,015 A | 4/1995 | Palermo |
| 5,411,466 A | 5/1995 | Hess |
| 5,425,720 A | 6/1995 | Rogalsky et al. |
| 5,429,582 A | 7/1995 | Williams |
| 5,484,384 A | 1/1996 | Fearnot |
| 5,498,227 A | 3/1996 | Mawad |
| 5,503,613 A | 4/1996 | Weinberger |
| 5,503,614 A | 4/1996 | Liprie |
| 5,532,122 A | 7/1996 | Drukier |
| 5,538,494 A | 7/1996 | Matsuda |
| 5,540,659 A | 7/1996 | Teirstein |
| 5,556,389 A | 9/1996 | Liprie |
| 5,575,749 A | 11/1996 | Liprie |
| 5,605,530 A | 2/1997 | Fischell et al. |
| 5,611,767 A | 3/1997 | Williams |
| 5,616,114 A | 4/1997 | Thornton et al. |
| 5,618,266 A | 4/1997 | Liprie |
| 5,624,372 A | 4/1997 | Liprie |
| 5,643,171 A | 7/1997 | Bradshaw et al. |
| 5,649,924 A | 7/1997 | Everett et al. |
| 5,653,683 A | 8/1997 | D'Andrea |
| 5,662,580 A | 9/1997 | Bradshaw et al. |
| 5,674,177 A | 10/1997 | Hehrlein et al. |
| 5,683,345 A | 11/1997 | Waksman et al. |
| 5,688,220 A | 11/1997 | Verin et al. |
| 5,707,332 A | 1/1998 | Weinberger |
| 5,713,828 A | 2/1998 | Coniglione .................. 600/7 |
| 5,720,717 A | 2/1998 | D'Andrea |
| 5,722,984 A | 3/1998 | Fischell et al. |
| 5,728,042 A | 3/1998 | Schwager |
| 5,730,698 A | 3/1998 | Fischell et al. |
| 5,782,740 A | 7/1998 | Schneiderman |
| 5,782,742 A | 7/1998 | Crocker et al. |
| 5,795,286 A | 8/1998 | Fischell et al. |
| 5,800,333 A | 9/1998 | Liprie |
| 5,803,895 A | 9/1998 | Kronholz et al. |
| 5,807,231 A | 9/1998 | Liprie |
| 5,816,259 A | 10/1998 | Rose |
| 5,816,999 A | 10/1998 | Bischoff et al. |
| 5,820,553 A | 10/1998 | Hughes |
| 5,833,593 A | 11/1998 | Liprie |
| 5,840,008 A | 11/1998 | Klein et al. |
| 5,840,009 A | 11/1998 | Fischell et al. |
| 5,840,064 A | 11/1998 | Liprie |
| 5,843,163 A | 12/1998 | Wall |
| 5,851,171 A | 12/1998 | Gasson |
| 5,851,172 A | 12/1998 | Bueche et al. |
| 5,855,546 A | 1/1999 | Hastings et al. |
| 5,857,956 A | 1/1999 | Liprie |
| 5,863,284 A | 1/1999 | Klein |
| 5,863,285 A | 1/1999 | Coletti |
| 5,865,720 A | 2/1999 | Hastings et al. |
| 5,871,436 A | 2/1999 | Eury |
| 5,871,437 A | 2/1999 | Alt |
| 5,873,811 A | 2/1999 | Wang et al. |
| 5,879,282 A | 3/1999 | Fischell et al. |
| 5,882,290 A | 3/1999 | Kume |
| 5,882,291 A | 3/1999 | Bradshaw et al. |
| 5,891,091 A | 4/1999 | Teirstein |
| 5,897,573 A | 4/1999 | Rosenthal et al. |
| 5,899,882 A | 5/1999 | Waksman et al. |
| 5,906,573 A | 5/1999 | Aretz |
| 5,910,101 A | 6/1999 | Andrews et al. |
| 5,910,102 A | 6/1999 | Hastings |
| 5,913,813 A | 6/1999 | Williams et al. |
| 5,916,143 A | 6/1999 | Apple et al. |
| 5,919,126 A | 7/1999 | Armini |
| 5,924,973 A | 7/1999 | Weinberger |
| 5,924,974 A * | 7/1999 | Loffler .................. 600/3 |
| 5,938,582 A | 8/1999 | Ciamacco, Jr. et al. |
| 5,947,889 A | 9/1999 | Hehrlein |
| 5,947,924 A | 9/1999 | Liprie |
| 5,947,958 A | 9/1999 | Woodard et al. |
| 5,957,829 A | 9/1999 | Thornton |
| 5,961,439 A | 10/1999 | Chernomorsky et al. |
| 5,967,966 A | 10/1999 | Kronholz et al. |
| 5,971,909 A | 10/1999 | Bradshaw et al. |
| 5,976,106 A | 11/1999 | Verin et al. |
| 5,997,462 A | 12/1999 | Loffler |
| 5,997,463 A | 12/1999 | Cutrer |
| 6,010,445 A | 1/2000 | Armini et al. .................. 600/3 |
| 6,010,446 A | 1/2000 | Grimm .................. 600/3 |
| 6,013,019 A | 1/2000 | Fischell et al. .................. 600/3 |
| 6,013,020 A | 1/2000 | Meloul et al. .................. 600/7 |
| 6,024,690 A | 2/2000 | Lee et al. .................. 600/3 |
| 6,030,333 A | 2/2000 | Sioshansi et al. .................. 600/3 |
| 6,033,357 A | 3/2000 | Ciezki et al. .................. 600/3 |
| 6,048,299 A | 4/2000 | Hoffmann .................. 600/3 |
| 6,090,035 A | 7/2000 | Campbell et al. |
| 6,099,455 A | 8/2000 | Columbo et al. |
| 6,106,454 A | 8/2000 | Berg et al. |
| 6,110,097 A | 8/2000 | Hastings et al. |
| 6,117,065 A | 9/2000 | Hastings et al. |
| 6,142,926 A | 11/2000 | Schneiderman |
| 6,146,322 A | 11/2000 | Papirov et al. |
| 6,149,574 A | 11/2000 | Trauthen et al. |
| 6,149,575 A | 11/2000 | Leonhardt |
| 6,152,869 A | 11/2000 | Park et al. |
| 6,162,165 A | 12/2000 | Apple et al. |
| 6,179,768 B1 | 1/2001 | Loffler et al. |
| 6,200,256 B1 | 3/2001 | Weinberger |
| 6,200,257 B1 | 3/2001 | Winkler |

| | | | |
|---|---|---|---|
| 6,200,307 B1 | 3/2001 | Kasinkas et al. | |
| 6,203,485 B1 | 3/2001 | Urick | |
| 6,213,976 B1 | 4/2001 | Trerotola | |
| 6,217,503 B1 | 4/2001 | Weinberger et al. | |
| 6,224,535 B1 | 5/2001 | Chiu et al. | |
| 6,224,536 B1 | 5/2001 | Pike | |
| 6,231,494 B1 | 5/2001 | Verin et al. | |
| 6,231,495 B1 | 5/2001 | Denk | |
| 6,231,719 B1 | 5/2001 | Garvey et al. | |
| 6,234,951 B1 | 5/2001 | Hastings | |
| 6,235,952 B1 | 5/2001 | Liprie | |
| 6,238,332 B1 | 5/2001 | Kanesaka | |
| 6,241,719 B1 | 6/2001 | Wallace et al. | |
| 6,248,057 B1 | 6/2001 | Mavity et al. | |
| 6,251,059 B1 | 6/2001 | Apple et al. | |
| 6,254,552 B1 | 7/2001 | Lewis et al. | |
| 6,258,019 B1 | 7/2001 | Verin et al. | |
| 6,261,219 B1 | 7/2001 | Meloul et al. | |
| 6,264,579 B1 | 7/2001 | Odai et al. | |
| 6,264,595 B1 | 7/2001 | Delfino et al. | |
| 6,264,596 B1 | 7/2001 | Weadock | |
| 6,264,598 B1 | 7/2001 | Armini | |
| 6,267,717 B1 | 7/2001 | Stoll et al. | |
| 6,267,775 B1 | 7/2001 | Clerc et al. | |
| 6,283,910 B1 | 9/2001 | Bradshaw et al. | |
| 6,283,911 B1 | 9/2001 | Keren | |

FOREIGN PATENT DOCUMENTS

| | | |
|---|---|---|
| DE | 197 24 233 C1 | 12/1998 |
| DE | 197 58 234 | 7/1999 |
| DE | 198 07 727 | 7/1999 |
| DE | 198 25 563 | 12/1999 |
| DE | 198 25 999 | 12/1999 |
| DE | 198 26 000 | 12/1999 |
| DE | 198 20 447 | 1/2000 |
| EP | 0 514 913 A2 | 11/1992 |
| EP | 0 633 041 A1 | 1/1995 |
| EP | 0 686 342 A1 | 12/1995 |
| EP | 0 688 580 A1 | 12/1995 |
| EP | 0 696 906 B1 | 2/1996 |
| EP | 0 749 764 A1 | 12/1996 |
| EP | 0 754 472 A2 | 1/1997 |
| EP | 0 754 473 A2 | 1/1997 |
| EP | 0 593 136 B1 | 3/1997 |
| EP | 0 778 051 A1 | 6/1997 |
| EP | 0 801 961 A2 | 10/1997 |
| EP | 0 810 004 | 12/1997 |
| EP | 0 813 894 A2 | 12/1997 |
| EP | 0 629 380 B1 | 7/1998 |
| EP | 0 865 803 | 9/1998 |
| EP | 0 904 798 | 3/1999 |
| EP | 0 904 799 | 3/1999 |
| JP | 10071210 | 3/1998 |
| JP | 2000024001 | 1/2000 |
| WO | WO 86/03124 | 6/1986 |
| WO | WO 93/04735 | 3/1993 |
| WO | WO 94/25106 | 11/1994 |
| WO | WO 94/26205 | 11/1994 |
| WO | WO 95/07732 | 3/1995 |
| WO | WO 96/06654 | 3/1996 |
| WO | WO 96/10436 | 4/1996 |
| WO | WO 96/13303 | 5/1996 |
| WO | WO 96/14898 | 5/1996 |
| WO | WO 96/17654 | 6/1996 |
| WO | WO 96/22121 | 7/1996 |
| WO | WO 96/29943 | 10/1996 |
| WO | WO 96/40352 | 12/1996 |
| WO | WO 97/07740 | 3/1997 |
| WO | WO 97/09937 | 3/1997 |
| WO | WO 97/17029 | 5/1997 |
| WO | WO 97/18012 | 5/1997 |
| WO | WO 97/19706 | 6/1997 |
| WO | WO 97/25102 | 7/1997 |
| WO | WO 97/25103 | 7/1997 |
| WO | WO 97/40889 | 11/1997 |
| WO | WO 98/01183 | 1/1998 |
| WO | WO 98/01184 | 1/1998 |
| WO | WO 98/01185 | 1/1998 |
| WO | WO 98/01186 | 1/1998 |
| WO | WO 98/11936 | 3/1998 |
| WO | WO 98/16151 | 4/1998 |
| WO | WO 98/20935 | 5/1998 |
| WO | WO 98/25674 | 6/1998 |
| WO | WO 98/29049 | 7/1998 |
| WO | WO 98/30273 | 7/1998 |
| WO | WO 98/34681 | 8/1998 |
| WO | WO 98/36788 | 8/1998 |
| WO | WO 98/36790 | 8/1998 |
| WO | WO 98/36796 | 8/1998 |
| WO | WO 98/39052 | 9/1998 |
| WO | WO 98/39062 | 9/1998 |
| WO | WO 98/39063 | 9/1998 |
| WO | WO 98/40032 | 9/1998 |
| WO | WO 98/46309 | 10/1998 |
| WO | WO 98/55179 | 12/1998 |
| WO | WO 98/55706 | 12/1998 |
| WO | WO 99/01179 | 1/1999 |
| WO | WO 99/02219 | 1/1999 |
| WO | WO 99/04706 | 2/1999 |
| WO | WO 99/04856 | 2/1999 |
| WO | WO 99/10045 | 3/1999 |
| WO | WO 99/21615 | 5/1999 |
| WO | WO 99/21616 | 5/1999 |
| WO | WO 99/22774 | 5/1999 |
| WO | WO 99/22775 | 5/1999 |
| WO | WO 99/22812 | 5/1999 |
| WO | WO 99/22815 | 5/1999 |
| WO | WO 99/24116 | 5/1999 |
| WO | WO 99/24117 | 5/1999 |
| WO | WO 99/29354 | 6/1999 |
| WO | WO 99/29370 | 6/1999 |
| WO | WO 99/29371 | 6/1999 |
| WO | WO 99/30779 | 6/1999 |
| WO | WO 99/34969 | 7/1999 |
| WO | WO 99/36121 | 7/1999 |
| WO | WO 99/39628 | 8/1999 |
| WO | WO 99/40962 | 8/1999 |
| WO | WO 99/40970 | 8/1999 |
| WO | WO 99/40971 | 8/1999 |
| WO | WO 99/40972 | 8/1999 |
| WO | WO 99/40973 | 8/1999 |
| WO | WO 99/40974 | 8/1999 |
| WO | WO 99/42162 | 8/1999 |
| WO | WO 99/42163 | 8/1999 |
| WO | WO 99/42177 | 8/1999 |
| WO | WO 99/44686 | 9/1999 |
| WO | WO 99/44687 | 9/1999 |
| WO | WO 99/49935 | 10/1999 |
| WO | WO 99/56825 | 11/1999 |
| WO | WO 99/56828 | 11/1999 |
| WO | WO 99/61107 | 12/1999 |
| WO | WO 99/62598 | 12/1999 |
| WO | WO 99/66979 | 12/1999 |
| WO | WO 00/03292 | 1/2000 |
| WO | WO 00/04838 | 2/2000 |
| WO | WO 00/04953 | 2/2000 |
| WO | WO 00/09212 | 2/2000 |
| WO | WO 00/32271 | 6/2000 |

| | | |
|---|---|---|
| WO | WO 00/45627 | 8/2000 |
| WO | WO 00/56249 | 9/2000 |
| WO | WO 00/69503 | 11/2000 |
| WO | WO 00/74778 | 12/2000 |
| WO | WO 00/76557 | 12/2000 |
| WO | WO 01/14011 A1 | 3/2001 |
| WO | WO 01/14617 A1 | 3/2001 |
| WO | WO 01/21106 A1 | 3/2001 |
| WO | WO 01/21245 A1 | 3/2001 |
| WO | WO 01/21248 A1 | 3/2001 |
| WO | WO 01/26734 A1 | 4/2001 |
| WO | WO 01/47602 A1 | 7/2001 |
| WO | WO 01/54764 A2 | 8/2001 |
| WO | WO 01/60443 A1 | 8/2001 |

OTHER PUBLICATIONS

*Radiotherapy of Intraoculare and Orbital Tumors,* Springer–Verlak publishers, Berlin Heidelberg and New York, copyright 1993, pp. 23–30 and 363–367.

Fackelmann, "Harbinger of a Heart Attack", *Science News,* vol. 151, Jun. 14, 1997, pp. 374–375.

Raloff, "Nuclear Medicine Gets Friendlier—Experimental Therapies Seek to Poison Just the Disease", *Science News,* vol. 152, Jul. 19, 1997, pp. 40–41.

Sutherland, "Managing Cancer Through Synergy", *Administrative Radiology Journal,* Nov. 1996, pp. 21–27.

* cited by examiner

Fig. 17

ELONGATED MEMBER FOR INTRAVASCULAR DELIVERY OF RADIATION

FIELD OF THE INVENTION

The present invention relates generally to intraluminal or intravascular catheters used to deliver radiation inside a living body. More specifically, the present invention relates to a radioactive source comprising an elongated wire.

BACKGROUND OF THE INVENTION

Intravascular diseases are commonly treated by relatively non-invasive techniques such as percutaneous transluminal angioplasty (PTA) and percutaneous transluminal coronary angioplasty (PTCA). These therapeutic techniques are well known in the art and typically involve use of a guide wire and a balloon catheter, possibly in combination with other intravascular devices. A typical balloon catheter has an elongated shaft with a balloon attached to a distal end and a manifold attached to a proximal end. In use, the balloon catheter is advanced over the guide wire such that the balloon is positioned adjacent a restriction in a diseased vessel. The balloon is then inflated and the restriction in the vessel is opened.

Vascular restrictions that have been dilated do not always remain open. In approximately 30% of the cases, a restriction reappears over a period of months. The mechanism of this restenosis is not understood. The mechanism is believed to be different from the mechanism that caused the original stenosis. It is believed that rapid proliferation of vascular smooth muscle cells surrounding the dilated region may be involved. Restenosis may be in part a healing response to the dilation, including the formation of scar tissue.

Intravascular radiation using a radioactive source has been proposed as a means to prevent or reduce the effects of restenosis. In particular, during or shortly after treatment, the blood vessel tissue concerned is irradiated with ionizing radiation, in particular $\beta$ and/or $\gamma$ radiation, so that a subsequent recanalization treatment is no longer necessary, or in any event, a much longer period of time elapses before such treatment is necessary.

In order to bring the radioactive source to the stretched blood vessel tissue, the source must be pushed, at least in part, through the catheter in the blood vessel. However, in many cases, the blood vessels, such as those of the coronary artery around the heart, comprise short or tight turns.

There is thus an on-going need to improve the design of radioactive sources used in intravascular treatments. The radioactive source should be flexible enough to permit displacement through a catheter in a blood vessel, while retaining sufficient stiffness to ensure that the radioactive material is positioned as desired for treatment.

SUMMARY OF THE INVENTION

A radioactive source for use in intravascular treatment includes an elongated support wire having a first diameter and an integral distal end having a second diameter. The second diameter is less than the first diameter. A spirally wound ribbon is disposed about the distal end. The ribbon is sheet-like having an outwardly facing major surface. The ribbon includes a radioactive material.

A second broad aspect of the present invention is a radioactive source that includes an elongated support wire having a first diameter and a distal end having a second diameter. The second diameter is less than the first diameter.

A plurality of spaced-apart toroidal elements are disposed on the distal end. Each toroidal element includes radioactive material.

A third broad aspect of the present invention is a radioactive source that includes an elongated support wire having a first diameter and a distal portion having a second diameter. The second diameter is less than the first diameter, and a radioactive material covering is provided over the distal portion.

DETAILED DESCRIPTION OF THE PREFERRED EMBODIMENTS

Figure 1:
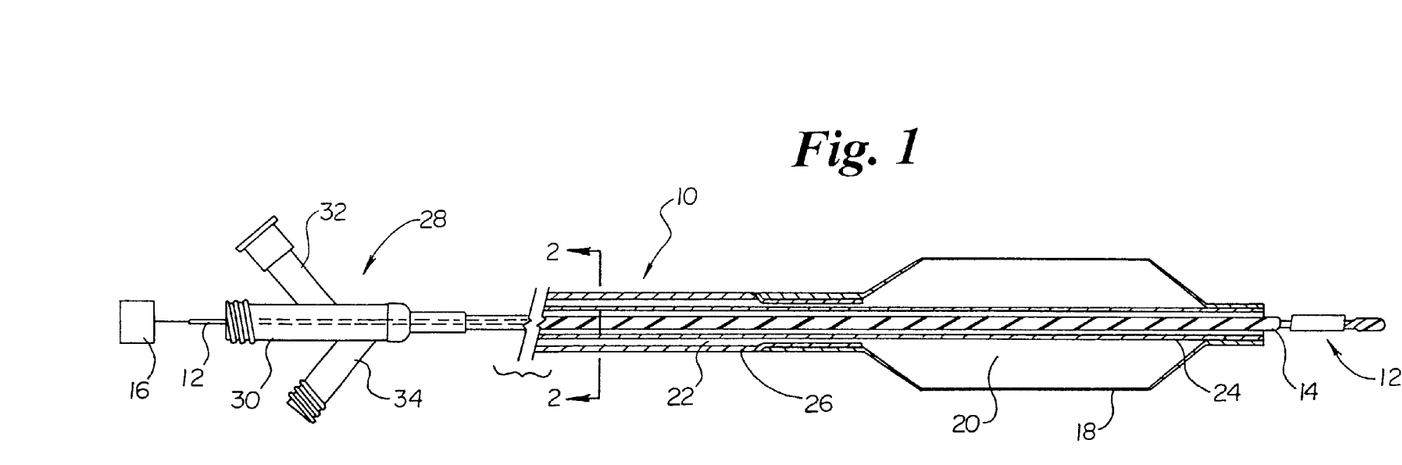
FIG. 1 is a partially sectioned side view of an exemplary catheter for use with the radiation source of the present invention.
Figure 2:
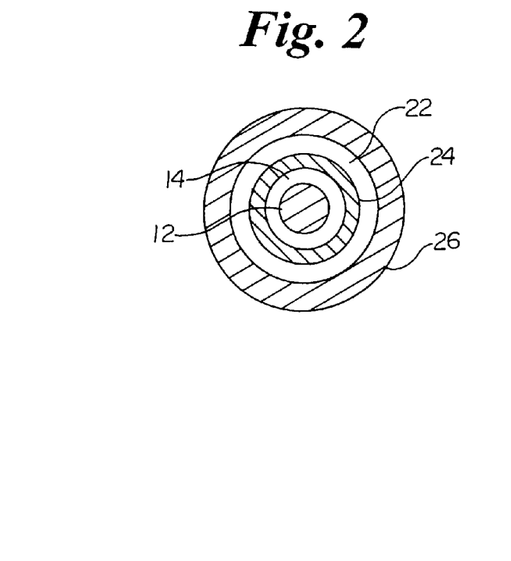
FIG. 2 is a cross-sectional view taken at 2—2 of FIG. 1.

FIGS. 1 and 2 illustrate an exemplary embodiment of a catheter 10 for receiving and delivering a radiation source 12 for intravascular treatment. Generally, the catheter 10 includes an open-ended lumen 14 extending therethrough. The elongated radiation source 12 is selectively disposed in the lumen 14, which is preferably closed-ended to prevent contamination of the radiation source 12. In one embodiment, an after-loader 16 connects to a proximal end of the radiation source 12 to advance and retract the radiation source 12 and safely contain it when not in use.

As illustrated, the catheter 10 includes an inflatable balloon 18 having an interior 20 which is in fluid communication with an inflation lumen 22. The catheter 10 illustrated in FIGS. 1 and 2 has a coaxial shaft construction including an inner tube 24 and an outer tube 26.

A manifold 28 connects to a proximal end of the catheter 10 and includes a guide wire port 30 and a flush port 32, both of which are in fluid communication with the open-ended lumen 14. The guide wire port 30 may include a toughy-borst (not shown) to seal about the proximal end of the radiation source 12. The manifold 28 also includes an inflation port 34, which is in fluid communication with the inflation lumen 22 and the interior 20 of the balloon 18.

It should be understood that the exemplary catheter 10 is but one suitable embodiment. Other catheter designs can be used to guide the radiation source 12 to the selected treatment area. For instance, non-concentric, dual lumen shaft designs can also be used.

Figure 3:
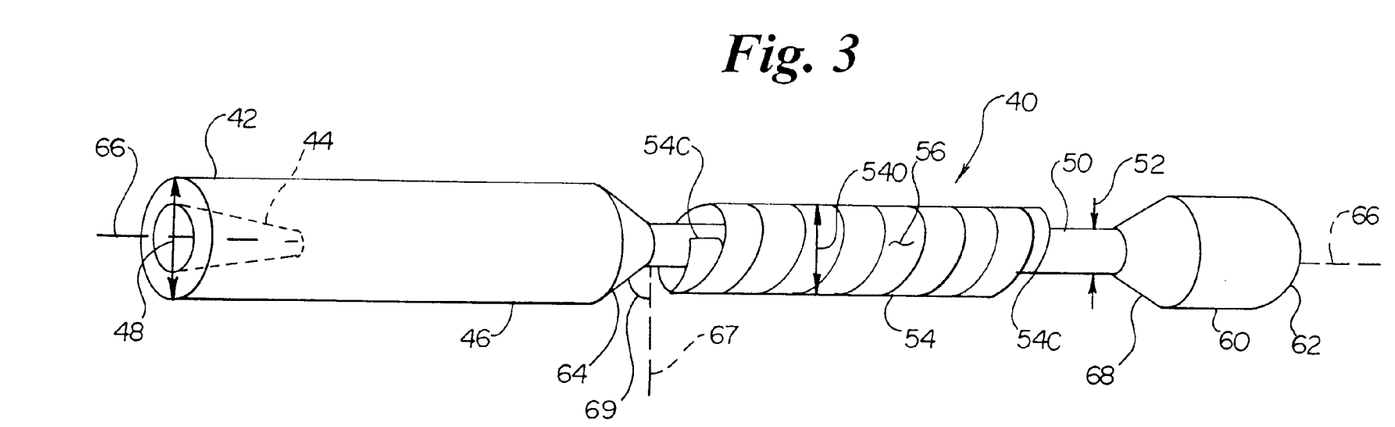
FIG. 3 is a perspective view of a distal end of the radiation source.

FIG. 3 is a perspective view of a first embodiment of a distal end 40 of the radiation source 12. Although the distal end 40 of the first embodiment and the other distal ends described below can be integrally formed as part of an end of a long wire (e.g., 100–300 centimeters, depending on the length of the catheter 10), other suitable embodiments, as illustrated, include an elongated support wire 48 having a proximal end 42 connectable to a second wire, not shown, of substantially longer length to form the complete radiation source 12. As appreciated by those skilled in the art, the distal end 40 can be attached to the second wire at the proximal end 42 using conventional welding, soldering, bonding or adhesive techniques. However, other methods of attachment, such as clamping or threading can also be used. The proximal end 42 can have a flat or planar surface for connection to the second wire, although commonly a male-female connection is used where the proximal end 42 can include a recess 44 of desired shape, such as conical, that receives a corresponding male end of the second wire. Alternatively, the proximal end 42 can include an extending male portion that is received in a corresponding recess of the second wire.

Generally, the distal end 40 of the radioactive source 12 includes the elongated support wire 46 having a first diameter 48 and an integral distal portion 50 having a second diameter 52, wherein the second diameter 52 is less than the first diameter 48. A spirally wound ribbon 54 is disposed about the distal portion 50. The ribbon 54 is sheet-like having an outwardly facing major surface 56. The ribbon 54 includes a radioactive material.

The elongated support wire 46 can be formed of materials well known to those skilled in the art, such as stainless steel, Nitinol, or the like. As stated above, the distal portion 50 is integrally formed as a single unitary body with the proximal end 42. Accordingly, distal portion 50 can be formed using conventional machine techniques, such as lathing or grinding. In another embodiment, the elongated support wire 46 may be molded using conventional molding methods.

In the illustrated embodiment, the elongated support wire 46 includes an enlarged end 60 on a remote end of the distal portion 50. In one embodiment, the enlarged end 60 has a diameter approximately equal to the first diameter 48. The enlarged end 60 can be a separate element securable to the elongated wire 48, or integrally formed with the elongated wire 48 as a single unitary body. Preferably, the enlarged end 60 has a rounded or atraumatic tip 62.

As also illustrated, the elongated support wire 46 can include a first taper transition portion 64 that extends from the first diameter 48 to the second diameter 52. The transition portion 64 can be formed with a conical surface disposed about a longitudinal axis 66 of the elongated support wire 48. The conical surface is defined by an angle of inclination 69 with respect to a reference line 67 perpendicular to the longitudinal axis 66. In one embodiment, the angle of inclination can be in the range from 0 degrees to 60 or 75 degrees. The transition portion 64 minimizes stress concentration associated with the change in diameter from the first diameter 48 to the second diameter 52. Likewise, a transition portion 68 can be provided to transition from the second diameter 52 to the diameter associated with the enlarged end 60. The second transition portion 68 is similar to the first transition portion 64.

Figure 4:
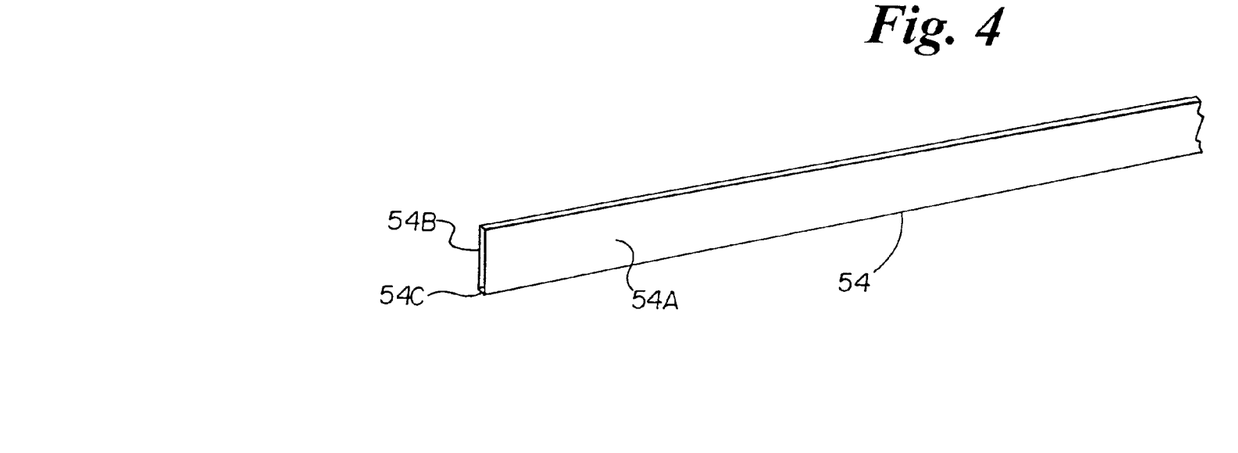
FIG. 4 is a perspective view of an elongated radioactive ribbon.

As stated above, the ribbon 54 is spirally wound about the distal portion 50. FIG. 4 illustrates the ribbon 54 prior to winding about the distal portion 50. The ribbon 54 can be formed of a solid, possibly compressed, radioisotope material. Alternatively, the ribbon can be formed of a core material, such as Nitinol, wherein a radioisotope is plated on one side 54A, or on both sides 54A and 54B of the ribbon 54. Wound surface 54A faces outwardly, while surface 54B faces inwardly. In one embodiment, the spirally wound ribbon 54 is formed in a tubular element, wherein edge portions of the wound ribbon are positioned substantially together.

Referring back to FIG. 4, ends 54C of the ribbon 54 can be secured to distal portion 50 in order to prevent contact with the inner walls or components of catheter components (lumen walls, balloons or the like), which can inhibit passage therethrough, particularly when transversing tight vascular bends. Preferably, an outer diameter 54D of the spirally wound ribbon is less than the first diameter 48.

Figure 5:
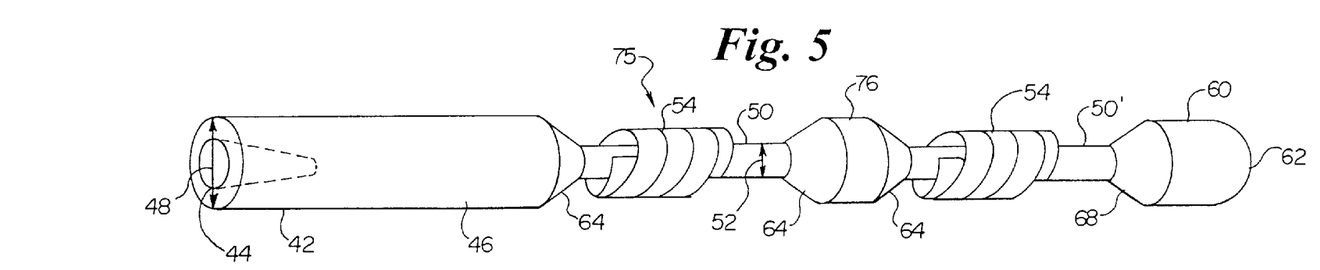
FIG. 5 is a perspective view of a radioactive source of the present invention having multiple sections.

FIG. 5 illustrates a distal end 75 comprising an elongated support wire 46 having a plurality of portions 50 and 50' separated by an intermediate section 76 of the first diameter 48. As illustrated, each of the portions 50 and 50' include a spirally wound ribbon 54 thereabout. Use of a plurality of portions 50 and 50' provides greater flexibility, allowing the radioactive source 12 to bend and traverse tight turns in blood vessels.

Figure 6:
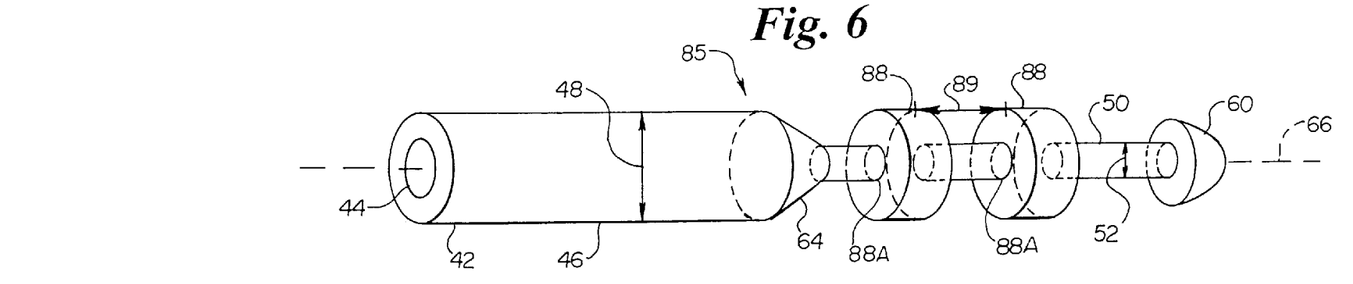
FIG. 6 is a perspective view of a radioactive source of the present invention having a plurality of spaced-apart toroidal elements.

FIG. 6 illustrates a third embodiment of a distal end 85 to form the radioactive source 12. In FIG. 6, the same reference numerals have been used to identify identical components of the previous embodiments. Generally, the distal end 85 includes the elongated support wire 46 having the first diameter 48 and the distal portion 50 having the second diameter 52. Preferably, the distal portion 50 is integrally formed with the proximal end 42. However, in this embodiment, a plurality of spaced-apart toroidal elements 88 are fixed in a stationary position on the distal portion 50, while in an alternative embodiment, one or all of the toroidal elements 88 include a corresponding bore 88A allowing toroidal element 88 to slide upon the distal portion 50. If fixed to the distal portion 50, toroidal elements 88 can be soldered, welded, glued, or the like using conventional securing techniques. Each toroidal element 88 contains radioactive material.

The spacing (as indicated by arrow 89) of the toroidal elements 88 provides increased flexibility. Preferably, the spacing 89 of the toroidal elements is sufficient to allow the distal portion 50 to conform around a bend having a diameter of 0.5 inches without plastic deformation. For example, in one embodiment, the spacing 89 between successive toroidal elements 88 is 1–5% of the longitudinal length of one of the toroidal elements 88. The longitudinal length being parallel to the longitudinal axis 66 of the elongated support wire 48. Increased spacing between successive toroidal elements 88 can provide greater flexibility. It should be noted that the spacing provided above can be fixed, wherein the toroidal elements 88 are fixedly secured to distal portion 50; or alternatively, the length of distal portion 50 is of sufficient length to provide the spacing distances listed above if the toroidal elements 88 can slide thereon.

Figure 7:
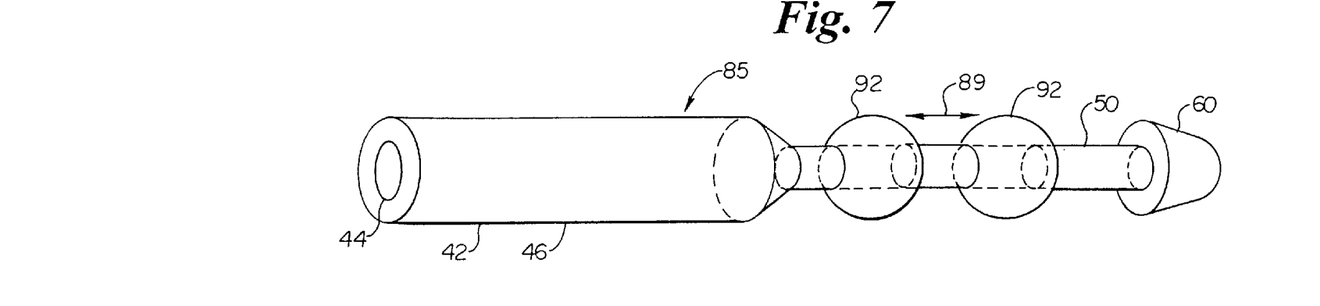
FIG. 7 is a perspective view of a radioactive source of the present invention having a plurality of spaced-apart toroidal elements of a second shape.

The outer shape of each of the toroidal elements 88 can take many forms such as a ring, sphere or the like. As used herein, a "toroidal element" includes each of these shapes. FIG. 7 illustrates toroidal elements 92 having a spherical outer shape. Generally, the outer shape is chosen to minimize sharp edges and to provide a desired radioactive emission pattern.

Figure 8:
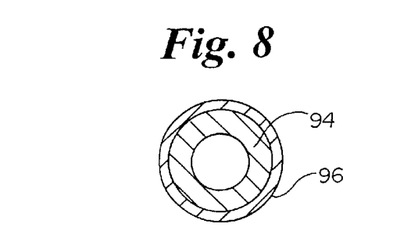
FIG. 8 is a sectional view of a first toroidal element.
Figure 9:
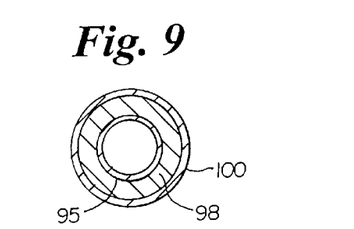
FIG. 9 is a sectional view of a second toroidal element.

FIG. 8 illustrates a first composition of a toroidal element, such as toroidal element 88, wherein a solid radioactive isotope core 94, such as ruthenium, is provided with a protective outer layer 96, such as gold. In an alternative embodiment illustrated in FIG. 9, a non-radioactive core 95, such as gold, is plated or covered with a radioactive material 98, such as ruthenium, which in turn is covered and capped by a plated protective outer layer 100, such as gold.

Figure 10:
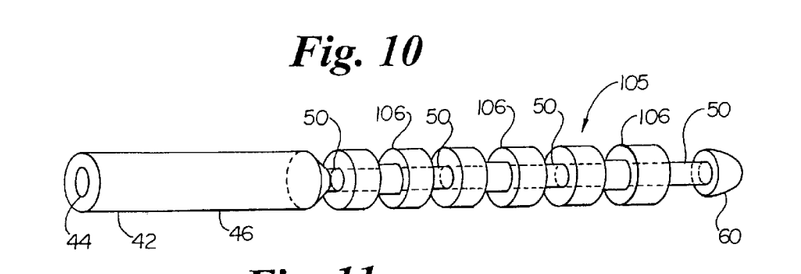
FIG. 10 is a perspective view of a radioactive source of the present invention having a plurality of spaced-apart toroidal elements of a third shape.
Figure 11:
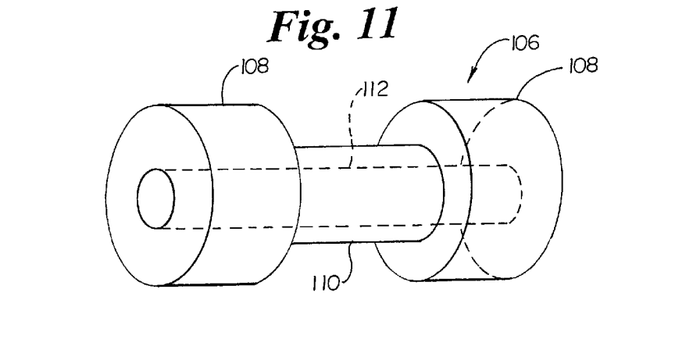
FIG. 11 is a perspective view of a toroidal element of the embodiment of FIG. 9.
Figure 12:
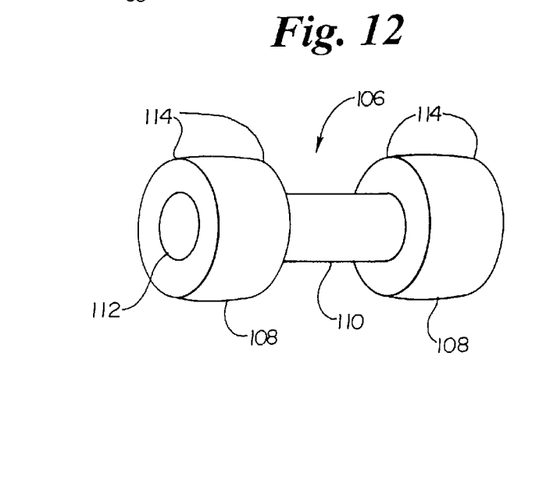
FIG. 12 is a perspective view of an alternative toroidal element.
Figure 13A:
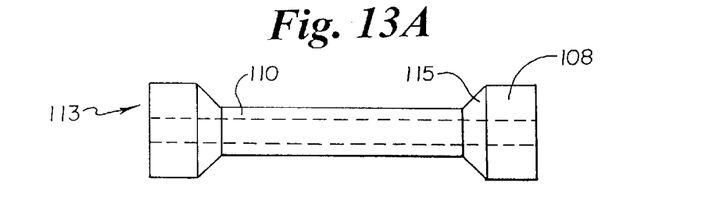
FIGS. 13A–13E are plan views of alternative toroidal elements of the embodiment of FIG. 9.
Figure 13B:
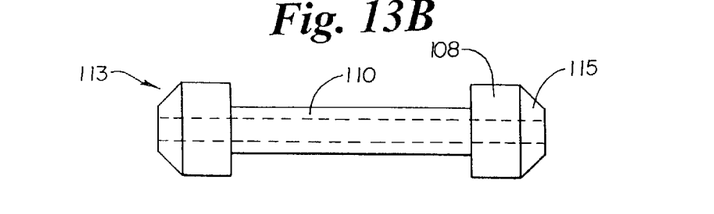
Figure 13C:
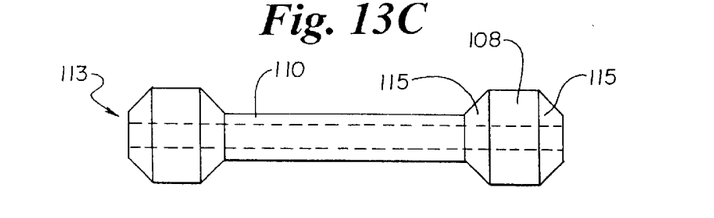
Figure 13D:
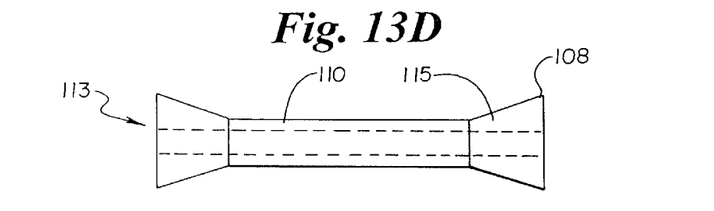
Figure 13E:
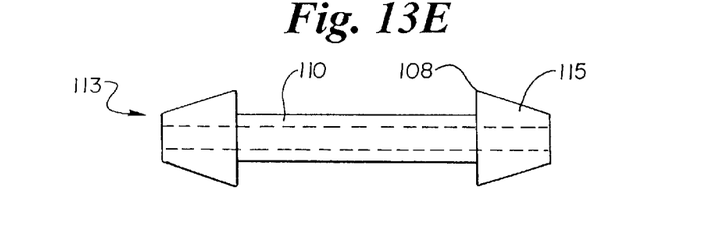

In FIG. 10, a distal end 105 includes a plurality of bar-bell shaped toroidal elements 106, which are illustrated in greater detail in FIGS. 11 and 12. Each toroidal element 106 includes enlarged end members 108 and a shaft portion 110 of reduced diameter connecting the enlarged end members 108. A center bore 112 extends through the toroidal element 106 and is of a size to receive distal portion 50. The number of toroidal elements 106 and a length of the distal portion 50 are selected so as to allow the toroidal elements 106 to be spaced-apart. As with the previous embodiments, the toroidal elements 106 can slide freely on the distal portion 50 or be secured thereto. In the embodiment illustrated in FIG. 12, edge portions 114 of the enlarged end members 108 are rounded or include an atraumatic radius so as to reduce sharp edges.

In the embodiments illustrated in FIGS. 10–12, radioactive material is located on the shaft portion 110, wherein the enlarged end members 108 protect the radioactive material from abrasion. In one embodiment, each toroidal element 106 can be formed from gold, which provides a good substrate for plating ruthenium thereon. A cap may be added for more protection, while retaining a recess. However, it is possible that no further protective layer is needed since the reduced diameter of the shaft portion 110 helps protect the radioactive material.

FIGS. 13A–13E illustrate alternative embodiments of the bar-bell shaped toroidal element 113. In these embodiments, each of the enlarged end members 108 include a conical transition portion 115 that tapers from the enlarged end members 108. The transient portion 115 may be linear as shown, or may be curved (e.g., parabolic). The radioactive material is disposed on the shaft portion 110. The transition portions 115 provide a buffer area for masking and/or reduce interference between each element 113 when loaded onto the distal portion 50. In particular, during manufacture, a mask is used to cover the circumference of the end members 108 and some of the transition portions 115 prior to deposition of the radioactive material, for example, via electroplating.

Figure 14:
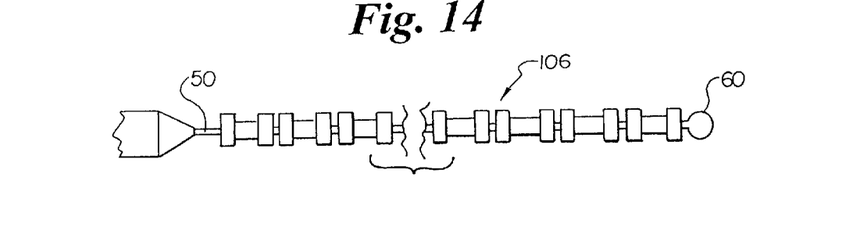
FIG. 14 is a plan view of the embodiment of FIG. 9 with an alternative end member.

FIG. 14 further illustrates that the enlarged end 60 can comprise a weld ball formed from a melted portion of the distal portion 50. In particular, after the toroidal elements 106, or any of the previous toroidal elements discussed above, have been disposed or threaded upon the distal portion 50, the end of the distal portion can be heated to form the enlarged end 60. If necessary, the enlarged end 60 can be ground, machined or polished to remove any sharp edges or excessive asymmetric shape.

Figure 15:
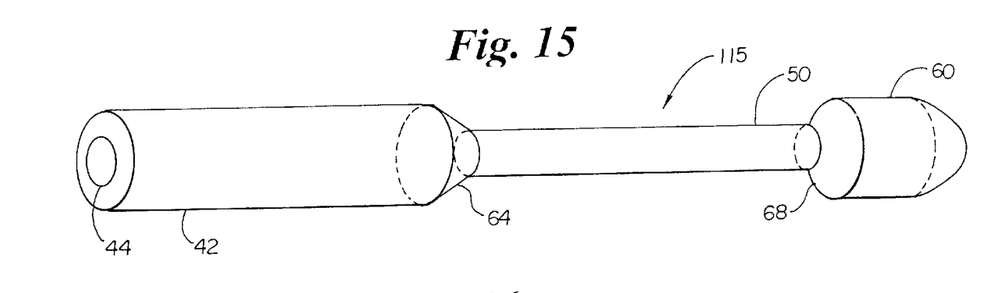
FIG. 15 is a perspective view of another radioactive source of the present invention.

In FIG. 15, a distal end 115 is formed to provide distal portion 50 in a manner similar to that described above. However, in this embodiment, radioactive material is disposed on distal portion 50, wherein the enlarged proximal end 42 and the enlarged end 60 protect the radioactive material from abrasion. Transition portions 64–68 are provided and masked with the proximal end 42 and the enlarged end 60 in a manner similar to the bar-bell toroidal element 113 described above so as to ensure radioactive material is deposited only on the distal portion 50. In a further embodiment, a protective outer layer, such as gold, is then provided over the radioactive material. The gold protective layer also improves radiopacity.

Figure 16:
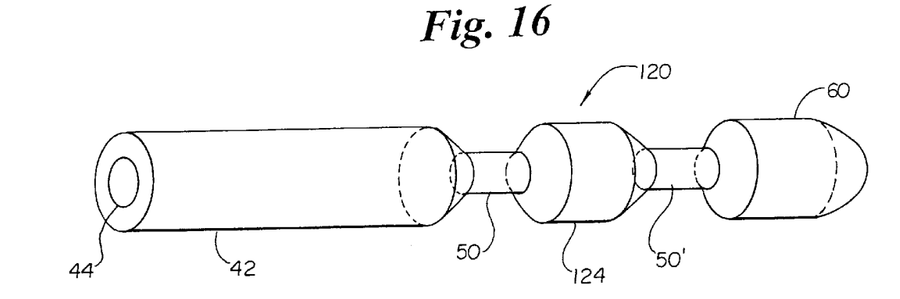
FIG. 16 is a perspective view of another radioactive source of the present invention.

In FIG. 16, distal end 120 includes a plurality of distal portions 50 and 50', wherein an intermediate member 124 is located therebetween. The intermediate member 124 has a diameter substantially equal to the proximal end 42 and the enlarged end 60. As with the embodiment of FIG. 15, radioactive material is disposed only on the reduced diameter distal portion 50 and 50'. Although illustrated wherein two reduced diameter distal portions 50 and 50' and a single intermediate member 124 are shown, it should be understood that additional distal portions and intermediate members 124 can be provided.

Figure 17:
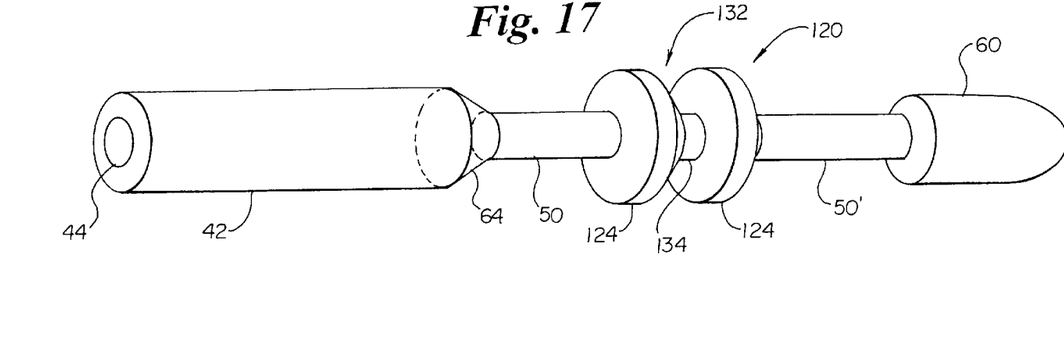
FIG. 17 is a perspective view of another radioactive source of the present invention.

In FIG. 17, distal end 120 further includes a flex link section 132 located between two successive intermediate members 124. The flex link section 132 is of a reduced diameter similar to the distal portions 50 and 50'. However, the flex link section 132 does not contain radioactive material and has a shaft portion 134 with a diameter that can be less than that of the distal portions 50 and 50' so as to improve flexibility.

Although the present invention has been described with reference to preferred embodiments, workers skilled in the art will recognize that changes may be made in form and detail without departing from the spirit and scope of the invention.

What is claimed is:

1. A radioactive source for use in intravascular treatment, the radioactive source comprising:

an elongated support wire having a first diameter and a distal portion having a second diameter, the second diameter being less than the first diameter; and a plurality of spaced-apart toroidal elements disposed on the distal portion, each toroidal element including radioactive material, wherein each of the toroidal elements is bar-bell shaped having a shaft portion and first and second enlarged end members on each end of the shaft portion.

2. The radioactive source of claim 1, wherein the radioactive material is disposed on the shaft portion of each toroidal element.

3. The radioactive source of claim 2, wherein the radioactive material is only disposed on the shaft portion of each toroidal element.

4. The radioactive source of claim 1, wherein each of the toroidal elements are fixed in a stationary position on the distal portion.

5. The radioactive source of claim 1, wherein each toroidal element includes a bore extending through the first end member, the shaft portion and the second end member, wherein the distal portion extends into the bore allowing the toroidal element to slide upon the distal portion.

6. The radioactive source of claim 5, wherein each of the toroidal elements are fixed in a stationary position on the distal portion.

7. The radioactive source of claim 1, wherein the first and second enlarged end members are substantially identical and include an outwardly facing circumferential surface defined by a radius from a center axis, wherein the radius is constant along and about the center axis.

8. The radioactive source of claim 1, wherein the first and second enlarged end members are substantially identical and include an outwardly facing circumferential surface defined by a radius from a center axis, wherein the radius is constant about the center axis but varies along the center axis.

9. The radioactive source of claim 1, wherein the toroidal elements are integral with the distal portion.

10. The radioactive source of claim 1, wherein each of the toroidal elements are fixed in a stationary position on the distal portion.

11. The radioactive source of claim 1, wherein each of the toroidal elements includes a bore allowing the toroidal element to slide upon the distal portion.

12. The radioactive source of claim 1, wherein the elongated support wire includes an enlarged end on a remote end of the distal portion.

13. The radioactive source of claim 12, wherein the enlarged end has a diameter approximately equal to the first diameter.

14. The radioactive source of claim 1, wherein each of the toroidal elements comprises a solid, compressed radioisotope.

15. The radioactive source of claim 14, wherein each of the toroidal elements includes a gold plating disposed on the radioisotope.

16. The radioactive source of claim 1, wherein each of the toroidal elements comprises a radioisotope layer on an outwardly facing major surface.

17. The radioactive source of claim 1, wherein the elongated support wire includes a tapered transition portion from the elongated support wire of the first diameter to the second diameter of the distal portion.

18. The radioactive source of claim 17, wherein the transition portion is formed with a conical surface disposed about a longitudinal axis of the elongated support wire, the conical surface defined by an angle of inclination with respect to a reference line perpendicular to the longitudinal axis in the range from greater than 0 degrees to less than 60 degrees.

* * * * *